United States Patent [19]

Schwartz, Jr. et al.

[11] 3,979,443
[45] *Sept. 7, 1976

[54] PROCESS FOR THE PREPARATION OF ESTERS OF MALEIC ACID WITH MONOHYDRIC ALCOHOLS

[75] Inventors: Andrew K. Schwartz, Jr.; Stone D. Cooley, both of Houston, Tex.

[73] Assignee: Petro-Tex Chemical Corporation, Houston, Tex.

[ * ] Notice: The portion of the term of this patent subsequent to Jan. 21, 1992, has been disclaimed.

[22] Filed: Aug. 25, 1972

[21] Appl. No.: 283,716

[52] U.S. Cl. .................. 260/485 R; 260/533 N; 260/346.8 M
[51] Int. Cl.² ..................................... C07C 69/60
[58] Field of Search ................ 260/485 R, 533 N

[56] References Cited
UNITED STATES PATENTS 2,683,110   7/1954   Rousseau ................. 260/346.8 R
3,094,539   6/1963   Bowman et al. ............. 260/533 N
3,527,677   9/1970   Harring .................... 260/533 N
3,862,147   1/1975   Cooley et al. ............. 260/485 R

OTHER PUBLICATIONS

Groggins, Unit Processes in Organic Synthesis, 4th edition; pp. 609–615, 622, 623, 630, 631, 636–638 (1952).

*Primary Examiner*—Jane S. Myers
*Attorney, Agent, or Firm*—N. Elton Dry; Kenneth H. Johnson

[57] ABSTRACT

Preparation of esters of maleic acid with monohydric alcohol by forming maleic anhydride by oxidizing a hydrocarbon in a maleic anhydride reaction, scrubbing the gaseous effluent to form aqueous maleic solution which is reacted and dehydrated in a first stage with monohydric alcohol in a distillation column. Reacting the product of the first stage under pressure and under conditions such that boiling occurs.

7 Claims, No Drawings

PROCESS FOR THE PREPARATION OF ESTERS OF MALEIC ACID WITH MONOHYDRIC ALCOHOLS

This invention relates to the preparation of esters of maleic acid with monohydric alcohols and to the preparation of monohydric esters of mixtures of maleic acid and fumaric acid. For various reasons maleic in the form of the anhydride is the principal starting material for maleic esters but the principal reason is because the anhydride is the form in which maleic is commercially produced. Maleic anhydride is commercially produced by the oxidation of hydrocarbons such as benzene or butene. Maleic anhydride is obtained by oxidizing the hydrocarbon feed at high temperature and over a suitable catalyst to produce a gaseous effluent of maleic anhydride together with impurities. The gaseous effluent is cooled and scrubbed in water to produce a crude solution of maleic acid. The aqueous solution of maleic acid is then fed to dehydration column in which the maleic acid is dehydrated by contacting with a volatile water insoluble entraining agent such as xylene which does not undergo chemical reaction in the system. The water and entraining agent are removed as overhead vapors and maleic anhydride is removed as bottoms.

According to this invention esters of maleic acid with monohydric alcohols are formed by (a) forming maleic anhydride by oxidizing a hydrocarbon in a maleic anhydride reactor to form a reactor effluent comprising gaseous maleic anhydride, (b) scrubbing said reactor effluent with water to produce a crude aqueous solution of maleic acid with said solution containing at least 40 percent by weight of water, (c) in a first stage reacting and dehydrating an aqueous solution of maleic acid with a monohydric alcohol in a distillation column with water being taken off overhead and a mixture comprising monohydric alcohol diesters and monoesters of maleic acid being taken off as a bottoms, (d) in a second stage reacting said mixture coming off as a bottoms from step (c) under a pressure of at least 25 p.s.i.g. and under conditions causing boiling of said mixture, and (e) recovering maleic acid esters from the product of step (d).

One of the objects of this invention is to prepare monohydric alcohol esters of maleic acid which are substantially or essentially water free starting from an aqueous maleic acid composition such as that obtained in the process of scrubbing maleic anhydride from the reactor effluent from a maleic plant. The preparation of the esters starting with the scrubber water solution of maleic acid offers several distinct advantages over the prior art methods of forming monohydric alcohol esters from purified maleic anhydride or maleic acid. A principal advantage is that it is not necessary according to this invention to dehydrate the maleic acid solution and further purify the maleic anhydride prior to esterification. According to this invention the production of fumaric acid is minimized, and further it has been discovered that the mixed alcohol esters of maleic acid and fumaric acid can be advantageously utilized. According to the prior art processes for producing maleic anhydride a considerable amount of maleic contents of the scrubber solution was converted to fumaric acid or was lost with the process water. Using the process of this invention high yields of maleic esters are produced at a low cost and pollution problems from the process are reduced. Maleic losses to the process water are also reduced because less maleic goes overhead with the water as compared to the prior art processes for dehydration of maleic acid to maleic anhydride.

In order to obtain the aqueous solution of maleic acid the gaseous vapor from the maleic anhydride reactor effluent containing the maleic anhydride are scrubbed with water. The maleic anhydride can be obtained by reacting benzene, n-butene, n-butane or other hydrocarbons and mixtures thereof by methods known in the art. The anhydride is converted to the acid and the impurities are dissolved and/or entrained in the water. This contact of the reactor effluent may be accomplished in any conventional manner and conventional equipment for gas/liquid mixing may be used such as scrubbers, turbo-absorbers, bubble or tray towers, absorbers, cascades, injector systems for recirculation through nozzle or towers and the like. At atmospheric pressure the typical temperature of the scrubber water will be about 20°C. to 90°C. with a preferred range being about 40°C. to 60°C. Both higher and lower temperatures may be used. Process for the oxidation of hydrocarbons to maleic anhydride, scrubbing of the maleic anhydride to produce an aqueous maleic acid solution and dehydration of the maleic acid to form maleic anhydride are known in the art and are described in Chemical and Engineering News, 38 (28) 1960; Encyclopedia of Polymer Science (1964); Kirk-Othmer Encyclopedia of Chemical Technology, 2nd. Ed., Vol. 12 828 (1967); U.S. Pat. No. 2,683,110 and U.S. Pat. No. 3,094,539 which are incorporated by reference.

The product discharge from the water scrubber preferably contains about 30 to 60 weight percent of maleic acid, with a preferred range being from about 35 – 45 weight percent maleic acid. The resultant crude maleic acid solution will generally contain other compounds such as fumaric acid as well as formaldehyde and related impurities depending upon the particular hydrocarbon fed to the reactor. Weak acids such as aliphatic or mono carboxylic acids of from 2 to 6 carbon atoms may be present. Aliphatic aldehydes of 2 to 6 carbon atoms may be present and there may be a variety of mixed tarry polymers such as from about 0.05 to 5 weight percent of the maleic acid.

If desired, the scrubber water may be pretreated to adjust for temperature, pressure or to remove certain impurities. However, it is one of the advantages of this invention that the maleic acid scrubber water can be conducted directly to the column. In the column the maleic acid solution is contacted with the monohydric alcohol at a temperature at least as high as the boiling point of the mixed composition; that is, under conditions such that boiling will occur. The boiling points of course will be influenced by pressure under which reaction takes place. In one embodiment of this invention the maleic acid solution is mixed with the monohydric alcohol in the stillpot of the distillation column and thereafter the mixture is heated to drive off water and monohydric alcohol during this initial stage of the reaction. A preferred method is to continuously feed maleic acid solution and the monohydric alcohol to the distillation column with the maleic acid solution being fed at a point lower than the monohydric alcohol. Preferably, the maleic anhydride will be fed to the upper two-thirds of the column and may be fed to the top of the column. The maleic acid solution may be fed to the spillpot but generally better results are obtained if the maleic acid solution is fed in the middle one-third of the distillation column. In the distillation column a mixture of monohydric alcohol and water comes off overhead and this may be separated by cooling in a condenser and decanting with the monohydric alcohol being recycled to the column and the water from the decanter being discharged. With most alcohols there will be some water present in the monohydric alcohol returned to the column and also some monohydric alcohol in the water phase which is discharged. The water layer from the decanter can be separated such as by distillation to recover monohydric alcohol which then may be recycled to the process.

The monohydric alcohols employed may be varied and may be such as primary, secondary or tertiary alcohols having from 1 to 18 carbon atoms with a preferred range being from 3 and preferably 4 to 8 carbon atoms. Normally, the tertiary alcohols are less desirable and the primary alcohols have given excellent results. Preferably the alcohol will not be completely soluble with water and also preferably the alcohol is one which will form a minimum boiling azeotrope with water. Saturated alcohols are preferred in order to avoid reactivity due to the unsaturation in unsaturated alcohols. Alcohols which can be separated by distillation from maleic acid esters of the same alcohol have been advantageously employed. Generally, the alcohols will have boiling points of from about 100 to 200°C. at atmospheric pressure. Examples of suitable alcohols are 1-propanol, 1-butanol, 2-buten-1-ol, 2-methyl-1-propanol, 1-hexanol, 1-octanol, 2-ethyl-1-hexanol, isooctyl alcohol, 1-decanol, isotridecyl alcohol, mixtures thereof and the like. Examples of mixtures of alcohols would be a mixture of 1-butanol and 2-butanol.

During this first stage of dehydration and esterification it is a feature of this invention that an excess of monohydric alcohol based on the combined mols of maleic acid and fumaric acid be employed. At least 2 mols of monohydric alcohol are preferably employed for each mol of maleic acid and fumaric acid in the aqueous solution but better results are obtained when this ratio is at least 2.2.

The pressure at the dehydration - esterification reaction may be varied and may be subatmospheric, atmospheric or above atmospheric pressure. The column will preferably be operated at about atmospheric pressure or greater up to e.g. 100 p.s.i.g. or greater. The temperature in the stillpot and in the overhead from the column will vary depending upon the particular monohydric alcohol being employed but the overhead temperature of the vapors from the column must be at least enough to cause boiling in the column and to cause water to be taken off overhead under the particular pressure conditions. Conventional esterification catalysts such as sulfuric acid or other esterification catalyst may be employed to promote the esterification but it is one of the advantages of this invention that esterification catalysts need not be employed. The dehydration-esterification column used for the first stage of reaction may be a fraction tower such as a sieve plate, bubble cap or packed tower with the feed points as indicated. The first stage of reaction is complete when the uncombined or free water has been essentially removed. This could be referred to as the water which was a solvent for the composition comprising maleic acid.

Taken off as bottoms from the column will be a mixture of mono and diesters of the monohydric alcohol with maleic acid, maleic anhydride and other reaction products and impurities depending on the composition of the maleic acid scrubber water fed to the column.

Generally, there will be both mono and diesters of the monohydric alcohol with fumaric acid. This composition is then reacted under pressure to form the esters. The pressure in this second stage should be at least 25 p.s.i.g. and suitably may be as high as 200 p.s.i.g. with a preferred range being between about 40 p.s.i.g. and 150 p.s.i.g. The temperature will also be increased to a temperature high enough to maintain boiling under the increased pressure. Generally, the temperature for this pressure reaction will be between about 100 and about 250°C in the stillpot with excellent results having been obtained within the range of 100° to about 230°C. The temperature and pressure for this reaction will be dependent somewhat on the monohydric alcohol chosen, the composition of the mixture in the stillpot and the like.

It is a feature of this invention that additional monohydric alcohol can be added prior to and/or during the second stage reaction. During this stage of the esterification process the total mols of monohydric alcohol should preferably be at least equivalent to the total number of free carboxylic groups in the mixture. This will take into account the mols of monoesters of maleic and fumaric acid present and the mols of maleic anhydride (equivalent to 2 carboxylic groups) and fumaric acid which are present and available for esterification. Preferably at least 1.1 mols of monohydric alcohol for each carboxylic group, or potentially carboxylic group in the case of the anhydride, will be utilized. The monohydric alcohol may be the same as or different from the monohydric alcohol added to the column during the first stage of reaction.

The second stage of the esterification process may be continued until the desired degree of esterification has been accomplished and may be measured by the acid number.

During the second stage reaction water formed by esterification can be taken off overhead. With most of the monohydric alcohols an azeotrope of water and alcohol will be taken off overhead. The overhead may be condensed and decanted with the alcohol suitably being returned to the stillpot or to the column for further reaction if desired. The second stage reaction may be conducted as a batch reaction at the end of the first stage reaction and the same or different equipment may be employed. Alternatively the stillpot mixture from the first stage reaction may be intermittently or continuously fed to separate equipment for the purpose of conducting the second stage reaction under pressure. This equipment may be any pressure reaction vessel but preferably will be of this type that will permit removal of water during esterification. Thus, the second stage may be a batch reaction or may be continuous or combinations of batch and continuous operation. If desired an esterification catalyst may be added to the second stage reaction.

The maleic and/or fumaric esters have known utilities and have been prepared and utilized for example as described in the Encyclopedia of Chemical Technology, Vol. 12 (Interscience, 1967), U.S. Pat. Nos. 2,644,009; 2,759,967; 2,766,273 and 3,418,363.

EXAMPLE I

The feed to the deydration process is crude maleic acid scrubber solution containing 41.6 percent maleic acid together with minor amounts of fumaric acid and impurities. This scrubber solution is obtained by the general process described in U.S. Pat. No. 2,683,110.

The first stage of the esterification and dehydration is conducted in a 4 inch internal diameter column consisting of lower and upper sections separated by a feed section. The lower unit is a glass Oldershaw 15 tray column. The upper unit is a 1.5 foot length of 4 inch diameter glass pipe containing 5 performated stainless steel trays. The reboiler is a section of 6 inch internal diameter glass pipe 20 inches in length which contains a multi-tube heat exchanger constructed of ¼ inch diameter stainless steel tubing. Steam at 150 psig is piped to the heat exchanger. The condenser and head above the column is designed so that the condensed liquid passes through a condensing chamber where the water phase is decanted and separated. The alcohol phase is continuously returned to the column. The stillpot is initially charged with 3798 g. of n-butanol and heated to refluxing. 4133 g of the 41.6 percent maleic acid solution is added to the column during 2 hours. The reaction is conducted at atmospheric pressure. The temperature of the overhead is about 94° – 102°C. during the run and the temperature of the stillpot is about 120° – 150°C. The crude product in the stillpot is refluxed for an additional 2 hours at a stillpot temperature of 158° – 170°C. The acid number of the product in the stillpot is 95.6.

1820 g. of the product of the first stage dehydration and esterification is mixed with 1403 g. of n-butanol alcohol to give a 50 percent by weight solution of the first stage product in n-butanol. This mixture is charged to the stillpot of a pressure distillation column. The column is pressurized with $N_2$ through a constant pressure regulator. The column has a 6 liter steel electrically heated stillpot and has a 9.5 ft. long distillation column of 1 inch internal diameter. The distillation column is steel and is packed with 316 stainless steel protruded hemicylinders 0.16 inch long (trade name Pro-Pack). The column is connected to an overhead condenser and an accumulator to allow separation of water with a pump to return reflux to the column. The column is externally heated and insulated. In this second stage of the esterification the pressure is initially 56 p.s.i.g. and is gradually reduced to 46 p.s.i.g. to maintain a stillpot temperature of 190°C. The ester product in the stillpot is refluxed for approximately 10 hours and the acid number of the material charged to the pressure distillation apparatus is reduced from 95.6 to essentially 0 during the run.

EXAMPLE 2.

The procedure of Example 1 is followed with certain exceptions. The stillpot of the first stage dehydration and esterification contained 4051 g. n-butanol. 4150 g. of crude maleic acid scrubber solution is added to the column during a 2 hour period. The crude product in the stillpot is refluxed for 11 hours after the addition of the scrubber solution is complete. The stillpot temperature is maintained at 155°–160°C. during this time after which the acid number of the crude product is 17.5. 1872 g. of the crude maleic reaction product having an acid number of 17.5 is charged to the pressure distillation apparatus. 1196 g of n-butanol is added to the stillpot. The charge is refluxed for 6-½ hours while removing an overhead of 550 g. The pressure during the distillation is held at 56 p.s.i.g. The stillpot temperature initially is 188°C. and rises to 193°C. during the run. At the end of the run, 2447 g of product is removed from the stillpot. The acid number of the final product is 0.12.

EXAMPLE 3

The procedure of Example 1 is followed with certain exceptions. The stillpot is charged initially with n-hexanol instead of n-butanol and refluxing is continued for 2 hours after addition of less than a stoichiometric amount of maleic acid in the scrubber solution. A portion of the crude product is diluted with n-hexanol in order to obtain a mixture about 50 percent by weight alcohol and is charged to the pressure distillation system. The mixture is refluxed under sufficient pressure to maintain a pot temperature of 190°C. for 10 hours with separation of water in the accumulator to form the ester product.

EXAMPLE 4

The procedure of Example 1 is repeated with the exception that the first and second stages of the reaction are conducted in the same apparatus which apparatus is the pressurized column of the second stage reaction of Example 1. Both the first and second stage reactions are conducted under a pressure of about 50 p.s.i.g. with the pressure varying somewhat during the stages.

The invention claimed is:
1. A process for the preparation of esters of monohydric alcohol with maleic acid which comprises
   a. forming maleic anhydride by oxidizing a hydrocarbon which is a precursor of maleic anhydride in a maleic anhydride reactor to form a reactor effluent comprising gaseous maleic anhydride
   b. scrubbing said reactor effluent with water to produce an aqueous solution of about 35 to 45 weight percent maleic acid, fumaric acid and at least 40 percent by weight of water
   c. in a first stage reacting and dehydrating said aqueous solution of maleic acid and fumaric acid with a primary monohydric alcohol having from 4 to 8 carbon atoms in a distillation column with solvent water being taken off overhead and a mixture comprising diesters and monoesters of maleic acid and esters of fumaric acid and said alcohol being taken off as a bottoms
   d. in a second stage reacting the said mixture from step (c) under conditions causing boiling and under a pressure of at least 25 p.s.i.g. to esterify substantially all of said acid.
2. The process of claim 1 wherein the monohydric alcohol has a boiling point from 100° to 200°C.
3. The process of claim 1 wherein the said monohydric alcohol is 1-butanol.
4. The process of claim 1 wherein the process is conducted in a distillation column wherein the said monohydric alcohol and the aqueous solution are fed to the distillation column and the monohydric alcohol is fed at a point higher in the column than the aqueous solution.
5. The process of claim 1 wherein the second stage reaction is accomplished in the stillpot of the same distillation column in which steps (a), (b) and (c) are conducted.
6. The process of claim 1 wherein additional monohydric alcohol is added to the product of step (c) prior to or during the said reaction according to step (d).
7. A process for the preparation of esters of maleic acid and n-butanol which comprises a. oxidizing a hydrocarbon which is a precursor of maleic anhydride to form a reactor effluent comprising maleic anhydride
b. scrubbing the said reactor effluent with water to obtain a crude aqueous solution consisting essentially of water, maleic acid and fumaric acid
c. feeding said crude aqueous solution to a refluxing distillation column while feeding n-butanol to said distillation column at a point higher in the column than the point of feed of the crude aqueous solution
d. taking off overhead from said distillation column an azeotrope of n-butanol and water while the said aqueous solution and n-butanol are being fed
e. separating the n-butanol-water mixture coming off overhead in step (d) and recycling at least a portion of the n-butanol to the distillation column
f. taking off as a bottoms from said distillation column an essentially water-free mixture of mono and diesters of n-butanol with maleic acid and fumaric acid
g. reacting said essentially water-free mixture under conditions such that the said mixture will boil and at a pressure of at least 25 p.s.i.g. while taking off water overhead from said distillation column to esterify substantially all of said maleic and fumaric acid.

* * * * *